United States Patent
Hufford et al.

(10) Patent No.: US 12,102,487 B2
(45) Date of Patent: *Oct. 1, 2024

(54) INSTRUMENT FOR OPTICAL TISSUE INTERROGATION

(71) Applicant: Asensus Surgical US, Inc., Durham, NC (US)

(72) Inventors: Kevin Andrew Hufford, Durham, NC (US); Matthew Robert Penny, Durham, NC (US)

(73) Assignee: Asensus Surgical US, Inc., Durham, NC (US)

( * ) Notice: Subject to any disclaimer, the term of this patent is extended or adjusted under 35 U.S.C. 154(b) by 277 days.

This patent is subject to a terminal disclaimer.

(21) Appl. No.: 17/563,949

(22) Filed: Dec. 28, 2021

(65) Prior Publication Data

US 2022/0117693 A1 Apr. 21, 2022

Related U.S. Application Data

(63) Continuation of application No. 15/917,898, filed on Mar. 12, 2018, now Pat. No. 11,259,892.

(Continued)

(51) Int. Cl.
*A61B 34/30* (2016.01)
*A61B 34/00* (2016.01)
*A61B 34/37* (2016.01)
*A61B 46/20* (2016.01)
*A61B 90/00* (2016.01)
*A61B 90/30* (2016.01)

(52) U.S. Cl.
CPC .............. *A61B 90/30* (2016.02); *A61B 34/37* (2016.02); *A61B 34/70* (2016.02); *A61B 46/20* (2016.02);

(Continued)

(58) Field of Classification Search
CPC ......... A61B 34/00; A61B 34/30; A61B 34/37; A61B 34/70; A61B 19/22; A61B 19/50;
(Continued)

(56) References Cited

U.S. PATENT DOCUMENTS 9,204,830 B2 12/2015 Zand et al.
11,259,892 B2* 3/2022 Hufford ................. A61B 46/10
(Continued)

FOREIGN PATENT DOCUMENTS

WO 2016056332 A1 4/2016
WO 2017031568 A1 3/2017

OTHER PUBLICATIONS

Brett, Peter N. et al., "Schemes for the Identification of Tissue Types and Boundaries at the Tool Point for Surgical Needles", IEEE Transactions on Information Technology in Biomedicine, vol. 4, No. 1, pp. 30-36 (Mar. 2000).

*Primary Examiner* — Vi X Nguyen

(57) ABSTRACT

A surgical system includes a light source, a sensor for detecting light, and a surgical device including an elongate shaft having a distal part positionable at a surgical working site within a body cavity. A first optical pathway transmits light from the light source to a distal part of the elongate shaft and onto tissue within the body cavity, and a second optical pathway receives light from tissue within the body cavity and transmits the received light to the sensor. A surgical barrier, such as one covering a robotic manipulator arm housing components of the system, is positioned such that at least the first or second optical pathway includes an optically transmissive portion of the surgical barrier.

12 Claims, 8 Drawing Sheets

Related U.S. Application Data

(60) Provisional application No. 62/470,125, filed on Mar. 10, 2017.

(52) U.S. Cl.
CPC ...... *A61B 90/361* (2016.02); *A61B 2090/306* (2016.02); *A61B 2562/00* (2013.01)

(58) Field of Classification Search
CPC . A61B 19/201; A61B 19/203; A61B 19/2203; A61B 90/30; A61B 90/361
See application file for complete search history.

(56) References Cited

U.S. PATENT DOCUMENTS

| | | |
|---|---|---|
| 2002/0150966 A1 | 10/2002 | Muraca |
| 2002/0161282 A1 | 10/2002 | Fulghum |
| 2004/0024288 A1 | 2/2004 | Uchikubo |
| 2006/0256191 A1 | 11/2006 | Iketani et al. |
| 2008/0177279 A1* | 7/2008 | Sumanaweera ...... A61N 5/1068 901/41 |
| 2009/0201577 A1 | 8/2009 | LaPlante et al. |
| 2011/0224574 A1 | 9/2011 | Sadler et al. |
| 2011/0234782 A1 | 9/2011 | Ehrhardt et al. |
| 2012/0156712 A1 | 6/2012 | Takats |
| 2012/0274631 A1 | 11/2012 | Friedland et al. |
| 2013/0296908 A1 | 11/2013 | Schulte et al. |
| 2014/0005483 A1 | 1/2014 | Ohashi et al. |
| 2014/0081659 A1 | 3/2014 | Nawana et al. |
| 2014/0188133 A1* | 7/2014 | Misener ............... A61B 8/0841 606/130 |
| 2015/0182107 A1 | 7/2015 | King et al. |
| 2015/0305811 A1 | 10/2015 | Neuberger |
| 2016/0100763 A1 | 4/2016 | Fengler et al. |
| 2016/0174848 A1 | 6/2016 | Ammar |
| 2019/0090969 A1 | 3/2019 | Jarc et al. |
| 2021/0065896 A1 | 3/2021 | Chiu et al. |

* cited by examiner

INSTRUMENT FOR OPTICAL TISSUE INTERROGATION

This application is a continuation of U.S. Ser. No. 15/917,898, filed Mar. 12, 2018, which claims the benefit of U.S. provisional application No. 62/470,125, filed Mar. 10, 2017.

FIELD OF THE INVENTION

The invention relates generally to use of optical interrogation for determining tissue information during a surgical procedure and communicating optical information to/from an instrument through a sterile drape.

BACKGROUND

There are several methods and systems for using multi- or hyper-spectral imaging for in vivo tissue diagnosis. These allow users to intra-operatively distinguish between different types of tissue, whether different organs, vessels or even cancerous versus benign tissue. Many of these techniques and systems are used in the endoscopic field as an alternative to biopsies.

There are various types of surgical robotic systems on the market or under development. Some surgical robotic systems use a plurality of robotic arms. Each arm carries a surgical instrument, or the camera used to capture images from within the body for display on a monitor. Other surgical robotic systems use a single arm that carries a plurality of instruments and a camera that extend into the body via a single incision. These types of robotic system use motors to position and orient the camera and instruments and, where applicable, to actuate the instruments. Input to the system is generated based on input from a surgeon positioned at master console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

This application describes configurations of surgical instruments having optical interrogation features, and configurations for using such instruments in surgical robotic systems.

DETAILED DESCRIPTION

This application describes surgical systems that make use of surgical instruments that can obtain information about body tissues in the operative working space during a surgical procedure. The tissue information is derived based on an optical interrogation means integrated into the surgical instrument. The tissue information can be used for tissue identification, tissue differentiation, diagnosis, and identification of fragile structures (nerves, ducts, blood vessels) prior to dissection or cauterization. In the case of cauterization, using optical interrogation to confirm the presence of a blood vessel between the jaws prior to cautery and to subsequently confirm hemostasis could improve the efficacy of cautery and minimize collateral tissue damage. Tissue information obtained using the instruments can be useful towards aiding the surgeon in creating adequate tumor margin when removing tumors in oncologic surgery, identifying cancerous lesions, identifying nerve or other fragile tissues or tissue structures prior to dissection. The optical interrogation function can be included on instruments having a treatment delivery mechanism such as therapeutic administration of optical energy. Optical energy administration may be used in combination with a suitable binding agent to enhance site-specificity.

Other types of tissue information that can be obtained or derived include tissue density, inflammation, ischemia, and blood vessel presence (via transmittance loss, hemoglobin detection, blood flow detection).

Figure 8:
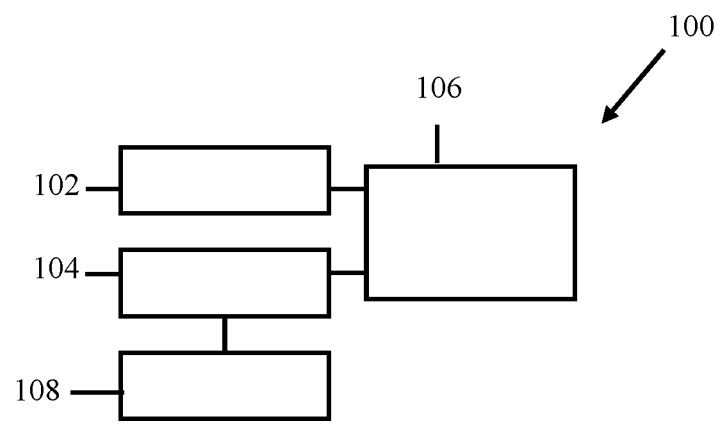
FIG. 8 is a schematic block diagram illustrating components of an exemplary surgical system according to the disclosed embodiments.

A surgical system 100 according to disclosed embodiments, shown schematically in FIG. 8, comprises a light source 102, a sensor 104 for detecting light, and a surgical instrument 106. The instrument includes a distal part positionable at a surgical working site within a body cavity, a first optical pathway for transmitting light from the light source to the distal part and onto tissue within the body cavity, and a second optical pathway for receiving light from tissue within the body cavity (light that is reflected or, in the case of some modalities such as fluorescence, emitted, from the tissue in response to illumination) and transmitting the received reflected/emitted light to the sensor 104. The system further includes a processor that receives from the sensor signals that are indicative of the light detected by the sensor. The processor is configured to analyze the signals to derive or determine tissue information using algorithms appropriate for the particular optical interrogation modality. The determined tissue information may be communicated to the user in a variety of ways, including those described in commonly-owned U.S. application Ser. No. 15/917,897 entitled COMMUNICATION OF DETECTED TISSUE CHARACTERIZATION IN A SURGICAL ROBOTIC PLATFORM filed on the same day as the present application.

The imaging means or sensor may be an image sensor, camera, or spectrometer. The sensor may be used for direct imaging of the region of interest, or in other types of sensing such as fluorescence imaging, time-resolved fluorescence spectroscopy, time-resolved infrared spectroscopy, diffuse-reflectance spectroscopy (DRS) which can be used for tissue differentiation, photoacoustic tomography (PAT), Raman spectroscopy, or optical coherence tomography (OCT)). In some embodiments, ultrasound or ultrasound elastography might be used in lieu of the optical modalities, or as an additional modality. Ultrasound elastography has been used, for example, to determine tissue information corresponding to the stiffness or elasticity of tissue. In instruments using ultrasound rather than optical modalities, the sensor is an ultrasound transducer rather than means for sensing light or electromagnetic radiation. Some instruments might be equipped for both optical interrogation and other interrogation modalities such as ultrasound.

The robotic surgical system may be of the types described in the Background section or another type of robotic system.

Figure 1A:
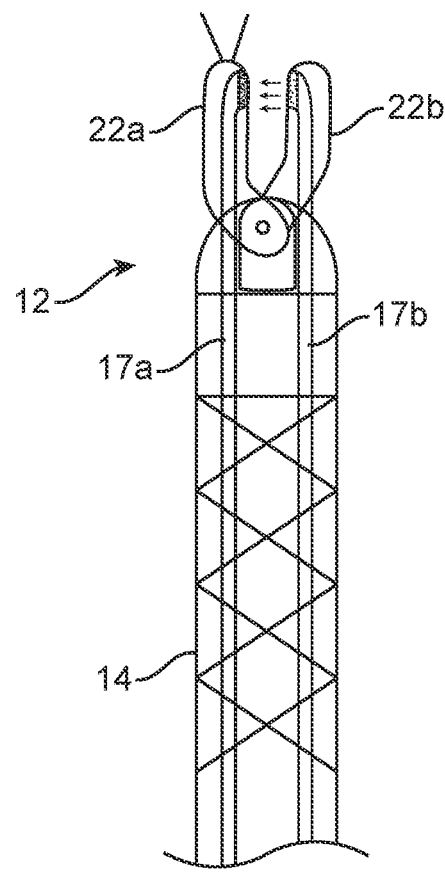
FIG. 1(a) illustrates a system including an instrument with sensing capabilities for optical interrogation of tissue. This embodiment is configured to optically transmit light through a surgical drape disposed between the fiber optics of the instrument and the light source and sensor components.

A first embodiment is shown in FIG. 1(a) and includes a surgical instrument having a distal part 12 and an elongate shaft 14. The system includes an optical module 15 comprising a source of light 16 (which may include one or more light sources) and a sensor 18 (which may optionally include a lens assembly 13). Light from the source 16 is transmitted to the distal part of the surgical instrument via an optical fiber or a bundle of optical fibers 17b, and light reflected or transmitted onto the tip of the instrument is transmitted to the image sensor 18 via an optical fiber or a bundle of optical fibers 17a running through the instrument shaft 14. An optional optical expander 11 is shown at the proximal end of the optical fiber cable 17a. Alternatives to this optical fiber configuration are discussed below in connection with FIGS. 4 and 5.

In this embodiment, the proximal part of the optical path (defined by the optical fibers/bundles and any associated optical expanders) is disposed on one side of a surgical drape 20, while the source 16 and sensor 18 are on the opposite side of the drape 20. In other words, light communicated from/to these fibers is transmitted through the drape 20. The drape may be constructed in its entirety of a material having suitable optically transmissive properties, or it might include a window formed of material having suitable optically transmissive properties.

Figure 1B:
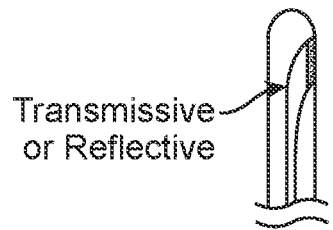
FIGS. 1(b), 1(c), 1(d) show alternate tip arrangements for the instrument of FIG. 1(a).
Figure 1C:
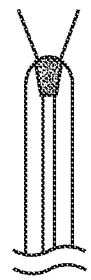

The distal part of the instrument may include jaw members 22a, 22b as shown. The distal ends of the optical fibers/bundles are exposed at the associated jaw member (optionally via an aperture in the jaw) or in optical communication with transmissive windows that are exposed in the jaw member. Transmission of light may be directed from one jaw towards the other jaw (see FIG. 1(b) and FIG. 1(d)), or it might be forward looking onto the tissue as in FIG. 1(c), or directed in another direction.

Figure 6:
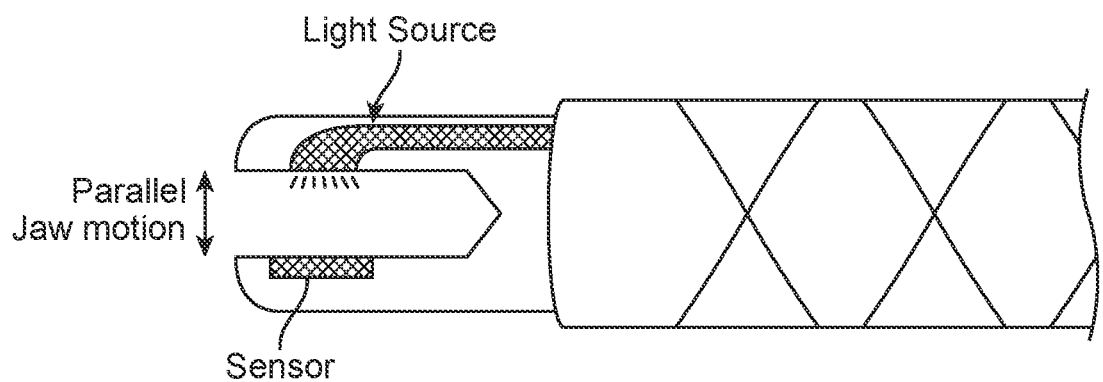
FIG. 6 shows an alternative embodiment of an instrument incorporating parallel jaw motion.

Accuracy of the optical interrogation may be enhanced by configuring the jaws to close in a parallel manner as shown in FIG. 6, with their separation distance (and thus the separation distance between the transmitting window/aperture and the receiving window/aperture) being known to a high degree of precision.

Figure 1D:
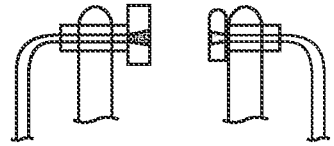

In a variation shown in FIG. 1(d), the optical fibers are clipped to or grasped by the jaw members, or clipped to a probe, rather than being integrated with the instrument. These fibers might extend down or along a trocar through which the instrument is passed, or down an external sleeve around the instrument. In these embodiments, the instrument or trocar may be reusable, or they might be disposable, saving instrument costs by allowing the use of reusable fiber optic components with disposable instruments.

The window/aperture for receiving reflected or transmitted light for transmission to the image sensor may be oriented towards the opposing jaw, or forward looking, or oriented in another direction. When both the light-receiving and light-transmitting apertures/windows faces the opposing jaw, tissue information can be obtained when the jaws are used to grasp tissue. Light is transmitted from jaw 22b into the grasped tissue. Light transmitted through the grasped tissue passes into the optical fiber(s) 17a of the other jaw 22a and are transmitted through the drape to the image sensor 18.

Figure 1E:
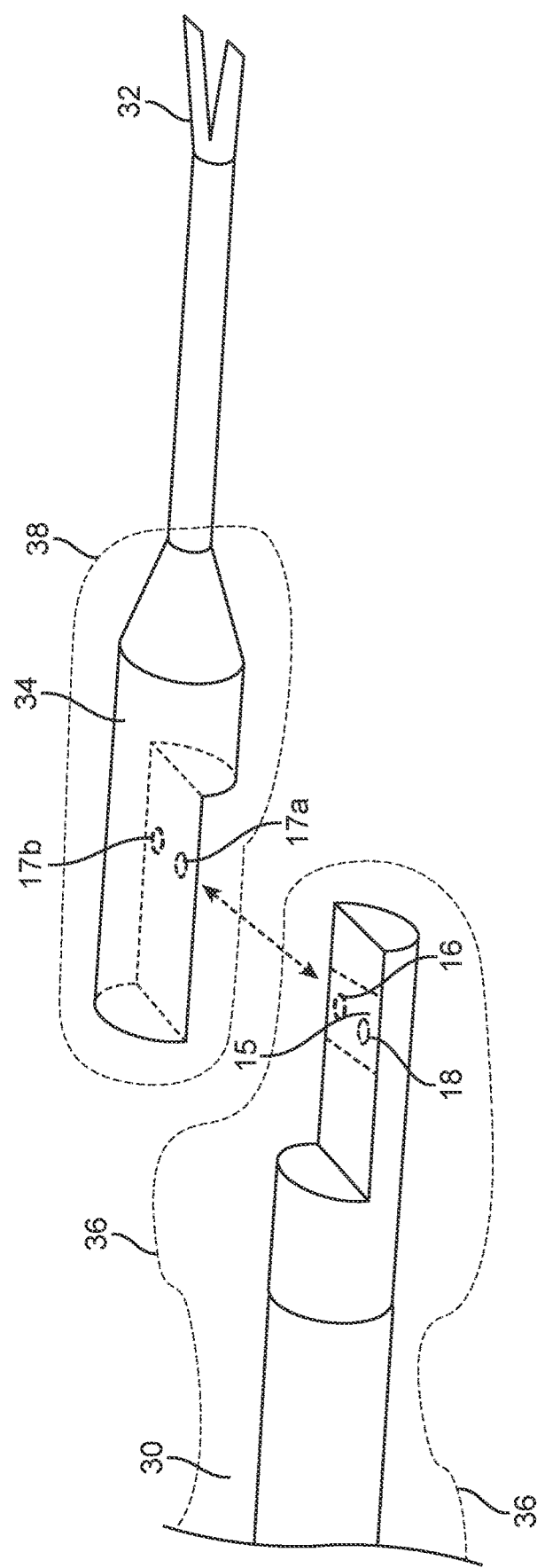
FIG. 1(e) shows the instrument of FIG. 1(a) incorporated into a robotic surgical system.

FIG. 1(e) shows an embodiment of the type shown in FIG. 1(a) adapted for use with a surgical robotic system similar to the Senhance™ Surgical System marketed by TransEnterix, Inc., Morrisville, NC The figure shows the distal portion of a robotic manipulator arm 30 which operates under the control of a command console (not shown) operated by the surgeon. The robotic manipulator has a terminal portion designed to support and operate a surgical device assembly 32. The surgical instrument 32 is removably mountable at its proximal housing 34 onto the manipulator arm 30. In this drawing, the surgical instrument 32 and the manipulator arm are shown separated to allow relevant features to be seen.

Sterile drapes are barriers are used to cover non-sterile components. The robotic arm 30 is typically provided non-sterile and thus is covered with a sterile drape 36. The surgical instrument (shaft and end effector) is provided as a sterile component, and in some cases the housing 34 of the surgical device assembly is also a sterile component and can be mounted directly onto the drape 36. In other cases, the housing 34 contains motors or sensitive electronics and thus cannot be subjected to sterilization processes. In those cases, a second sterile barrier 38 such as a sterile bag is positioned around the housing 34 before it is mounted onto the robotic arm. Motion to actuate features of the surgical instrument (e.g. jaw open-close, bending or articulation) may be driven by motors in the arm and mechanically transmitted across the drape, and/or it may be driven by motors in the housing. Other features of the system are found in US 20160058513, U.S. Pat. Nos. 9,350,934, 9,358,682 and US 2013/0012930.

A source of light 16 and an optical sensor 18 are positioned on the arm. These components might be integral with the arm or they might be components of an optical module 15 removably positioned on the manipulator arm 30. Power for these components may be provided via the manipulator arm.

The instrument may be configured as described with respect to FIGS. 1(a)-1(d). During use, the housing 34 of the surgical instrument is mounted on the manipulator arm 30. When optical interrogation is to be carried out, light from the source 16 is transmitted across the one or more sterile barriers 36, 38 and is received by an optical fiber or a bundle of optical fibers 17b which carry the light to the distal part of the surgical instrument 32. Light reflected or transmitted onto the tip of the instrument is received by an optical fiber or a bundle of optical fibers 17a running through the instrument shaft and is transmitted to the image sensor 18. The drape(s) may be constructed in its entirety of a material having suitable optically transmissive properties, or it might include a window formed of material having suitable optically transmissive properties.

While some embodiments use jaws, other embodiments do not include jaws; others may include jaws but use only one jaw in the performance of the optical interrogation methods described here. In these embodiments, both apertures/windows are on a single probe or jaw and arranged so that light from the light-emitting aperture/window is reflected off of tissue in the operative site and reflected light passes into the light-receiving aperture/window for communication to the image sensor (or, in the case of fluorescence, light is absorbed by tissue and light subsequently emitted by the tissue is received into the light-receiving window/aperture).

In still other embodiments, the illumination element and the receiving element are on different devices. For example, light may be emitted locally by the instrument but received by another device such as the endoscope, the trocar, or another device, or light may be emitted by a separate device and received by the surgical instrument.

Figure 2:
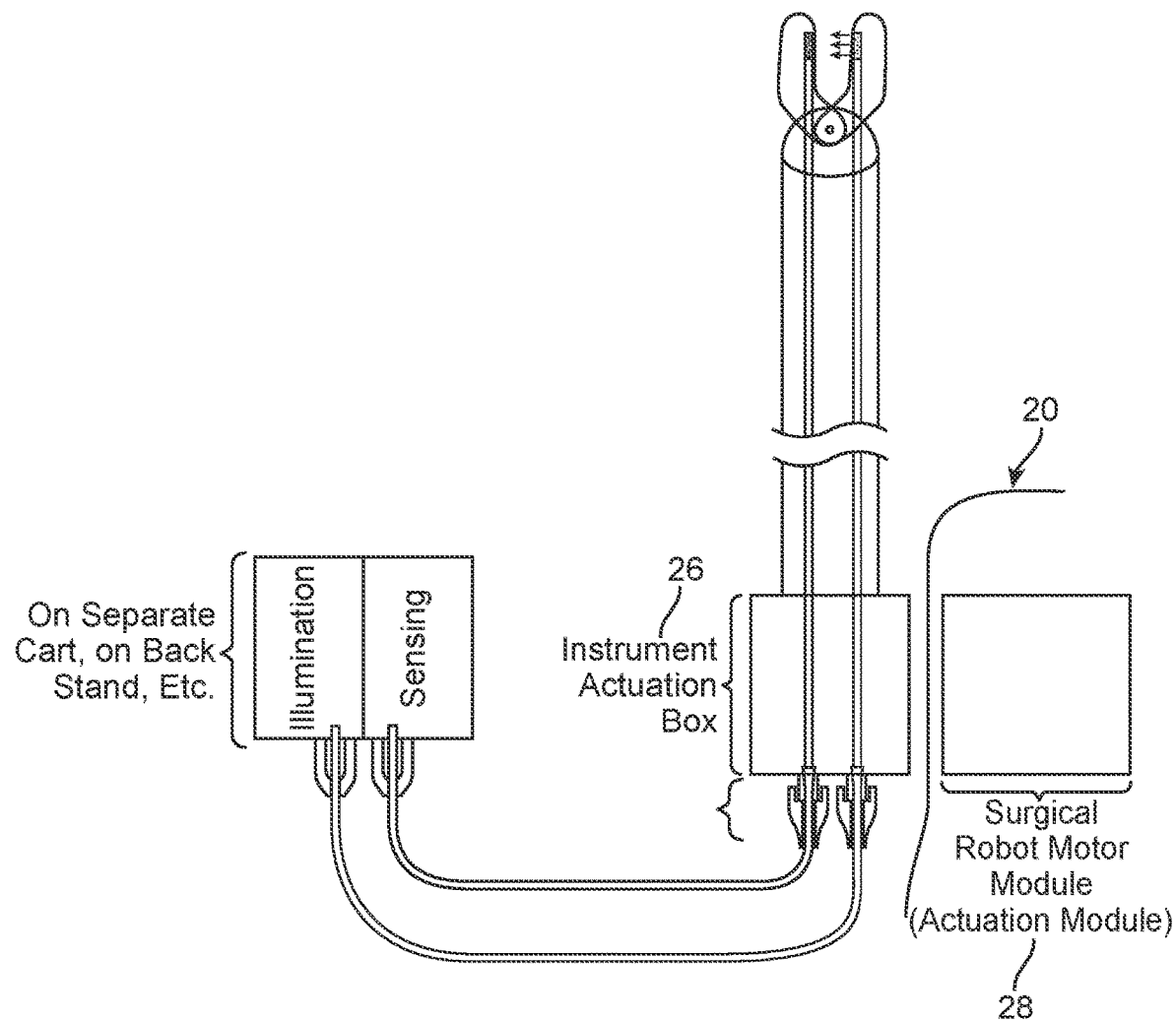
FIG. 2 illustrates a second embodiment of a system including an instrument with sensing capabilities for optical interrogation of tissue, including one or more remote module(s) connected by cables to the instrument and housing the light source and sensor.

In a second embodiment shown in FIG. 2, optical interrogation is integrated into a robotically controlled surgical instrument in an alternative configuration. In this embodiment, the light-transmitting fibers (which carry the light used to illuminate tissue away from the light source) and the light-receiving fibers (which carry light received from the tissue towards the sensor) are attached using fiber optic cables to the respective modules that house the illumination source and the image sensor. The cables extend from a proximal part of the surgical instrument and/or are attached to the proximal part of the instrument using fiber optic couplers. In the drawing, an instrument actuation assembly 26 at the proximal part of the instrument includes couplings for receiving the distal ends of the cables as shown. In a slight modification to this embodiment, fiber optic connectors are used for either the connection between light source and its associated light-transmitting fibers or for the connection between the sensor and its associated light-receiving fibers. The other connection is made via transmission through the drape in a manner similar to that shown in FIG. 1(a).

The instrument shaft may be one of a variety of types that may have its position and/or orientation controlled by actuators of the robotic surgical system. Exemplary shaft types include rigid shafts, continuum robotic or bendable shafts, shafts having discrete articulating joints, or shafts with articulating wrists or other articulating elements. The robotic system may be one that communicates motion from drive mechanisms of an actuation drive assembly (motor module) 28 disposed on one side of a surgical drape 20 to driven mechanisms of the instrument in the instrument actuation assembly 26. One such configuration is shown in published PCT Application No. WO 2016/057989 which is incorporated herein by reference.

Figure 3:
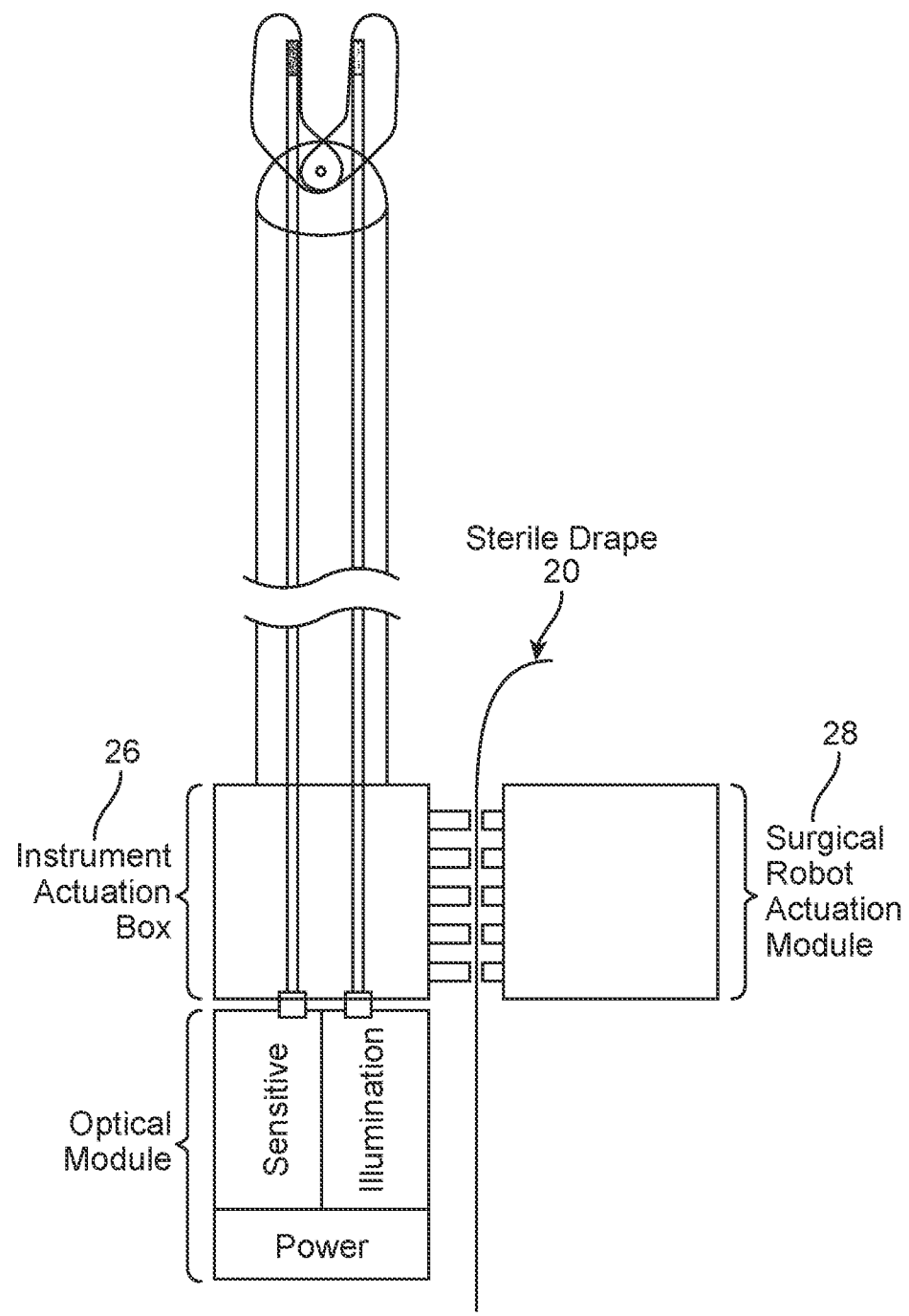
FIG. 3 illustrates a third embodiment of system including an instrument with sensing capabilities for optical interrogation of tissue, including an optical module carried by the instrument.

The FIG. 3 embodiment also shows integration of optical interrogation into a robotically controlled surgical instrument. In this embodiment, the light source and sensor components are separate from the instrument, and may be in one or two modules or housings that mount to a part of the instrument, such as at the actuation assembly 26. A battery pack may be used to supply power to the interrogation system. As in the FIG. 2 embodiment, the surgical robotic actuation drive assembly 28 may be one that communicates motion through the drape, allowing the motor module to remain outside the sterile field.

The illumination and/or sensing may be carried out using instrument types other than those shown in the drawings. For example, a trocar positionable in an incision for receiving surgical instruments may be equipped to illuminate the tissue and/or communicate the light reflected or transmitted from the tissue or fluorescent agent to the sensor.

Figure 4:
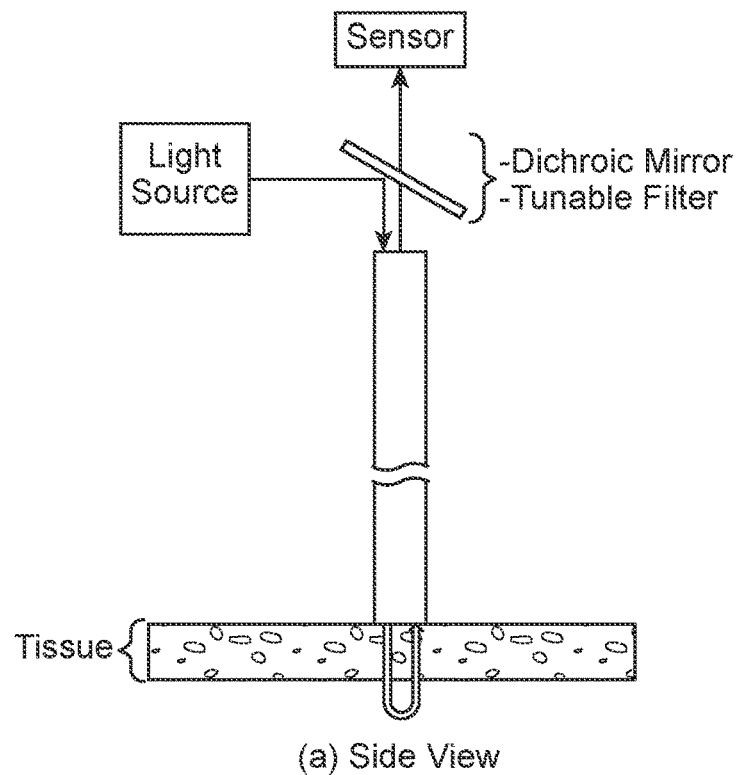
FIG. 4 shows an arrangement of optical components that may be used in instruments of the type described herein to allow light for illuminating and sensing to be carried by the same optical fiber.
Figure 5:
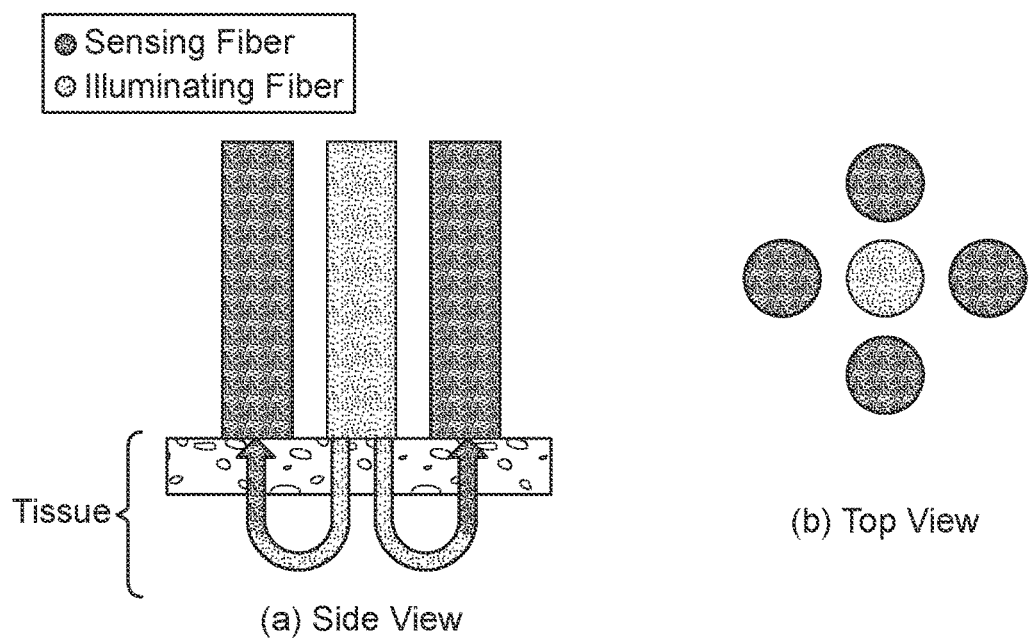
FIG. 5 shows an arrangement of optical fibers that may be used in instruments of the type described herein.

FIGS. 4 and 5 show alternatives to the optical fiber configurations discussed above. In FIG. 4, a single optical fiber is used as both the light-transmitting fiber and the light-receiving fiber. This embodiment makes use of a dichroic mirror or tunable filter to create the appropriate pathways for each type of light, as shown. This embodiment may be particularly suitable where the optical interrogation relies on administration to tissue of a fluorescent agent that fluoresces at a wavelength that is different from the illumination wavelength emitted by the light source. The dichroic mirror or tunable filter can be configured to reflect light from the light source into the optical fiber, and to transmit light from the optical fiber through the mirror/filter onto the sensor. In a variation of this embodiment, the arrangement of the light source and sensor are reversed (with a corresponding reconfiguration of the dichroic mirror/tunable filter).

FIG. 5 shows a fiber arrangement that carries out both reflectance and transmittance, including diffuse-reflectance spectroscopy (DRS). In the embodiment that is shown, the fiber arrangement for the instrument includes a light-transmitting or "illuminating" fiber that transmits light to the tissue, and a plurality of light-receiving or "sensing" fibers. The ratio of illuminating fibers to sensing fibers might be 1:1 up to 1:many. The fibers may run adjacent to one another as shown. A modification of this embodiment uses broad area illumination in combination with multiple sensing fibers. In still other embodiments, the sensing fiber(s) are arranged to obtain reflected light from a single spot of interest, an area of interest, or multiple points of an area (similar to an imaging approach).

In other embodiments, the number and arrangement of illuminating fibers relative to the sensing fibers may be reversed from what is described with respect to FIG. 5, with the illuminating fibers taking the place of the sensing fibers and vice versa.

Figure 7:
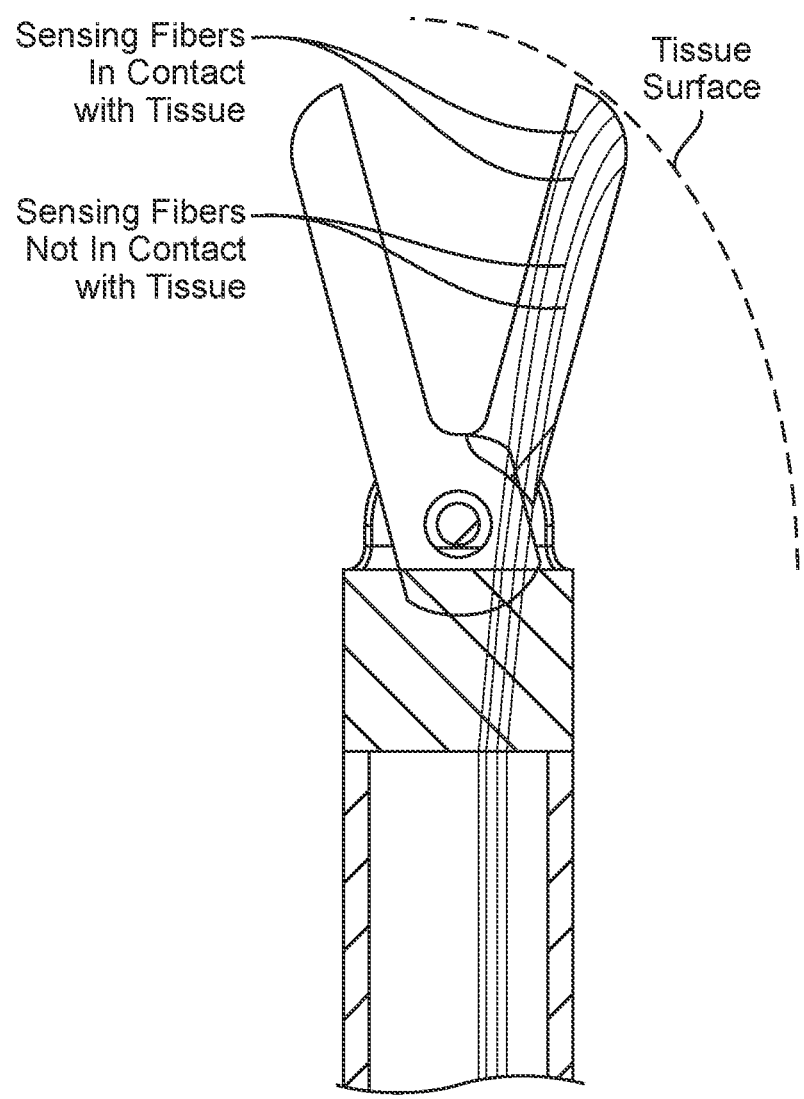
FIG. 7 shows an alternative embodiment configured to provide information along the edges of a surgical instrument.

FIG. 7 shows an optical interrogation instrument 40 used to conduct interrogation of tissue along an edge or tip of a surgical instrument. In the illustrated embodiment, the instrument includes a pair of jaw members 42. At least one of the jaw members includes at least one optical sensing fiber which conducts light to a detector. The sensing fibers are arranged to detect light from a single point of measurement, multiple discrete measurement points, or a continuous measurement or feedback area. The light emitter may also be on the jaw member or it may be on a separate instrument such as a trocar that receives the instrument 40 or a separate instrument. In other embodiments, the jaw member will include the light emitter only, in which case the light detector is positioned on a separate instrument. As can be seen in the drawing, these elements are positioned so that receipt of reflected light occurs along the exterior edge of the jaw (as opposed to the edge that opposes the other jaw), allowing for tissue interrogation when the exterior edge contacts tissue during blunt dissection. In modified versions of the FIG. 7 embodiment, the jaw members are replaced with another type of instrument such as a probe such as, for example, a monopolar dissecting hook. Information obtained using this device may be communicated to the user in the manner described in commonly-owned U.S. application Ser. No. 15/917,897, or in another way.

All patents and patent applications referred to herein, including for purposes of priority, are incorporated herein by reference.

What is claimed is:

1. A surgical method comprising:
removably positioning a sterile barrier on a manipulator arm;
removably positioning a surgical instrument on the manipulator arm such that the sterile barrier is positioned between a portion of the manipulator arm and a portion of the surgical instrument;
introducing a distal end of the surgical instrument into a body cavity, and positioning a portion of tissue between first and second jaw members of the surgical instrument,
transmitting light to the portion of tissue from a first optical fiber having a distal end exposed on the first jaw member,
receiving light from the portion of tissue at a second optical fiber having a distal end exposed on the second jaw member, and transmitting the received light to a sensor.

2. The method of claim 1, further comprising:
removably positioning a sterile barrier on a manipulator arm, the sterile barrier having an optically transmissive portion;
removably positioning the surgical instrument on the manipulator arm such that the sterile barrier is positioned between a portion of the manipulator arm and a portion of the surgical instrument;
wherein transmitting light to the tissue from the first optical fiber includes transmitting light from the manipulator arm across the optically transmissive portion of the barrier to the first optical fiber.

3. The method of claim 2, wherein the light source is positioned on the manipulator arm, and wherein removably positioning the sterile barrier on the manipulator arm includes positioning the sterile barrier with the optically transmissive portion covering at least a portion of the light source.

4. The method of claim 2, wherein the optically transmissive portion of the barrier is a window in the barrier formed of optically transmissive material.

5. The method of claim 2, wherein the barrier is constructed in its entirety of optically transmissive material.

6. The method of claim 2, wherein the sensor is disposed on the manipulator arm, and wherein receiving light from the portion of tissue and transmitting the received light to the sensor includes transmitting the received light across the sterile barrier to the sensor.

7. The method of claim 2, further including using the first or second optical fiber to deliver optical treatment energy.

8. The method of claim 1, wherein a processor receives from the sensor signals that are indicative of the light detected by the sensor and analyzes the signals to derive or determine tissue information.

9. The method of claim 8, wherein the tissue information is tissue differentiation information, tissue type information, tissue density information, tissue pathology information, or information indicating inflammation, ischemia, or blood vessel presence (via transmittance loss, hemoglobin detection, or blood flow detection).

10. The method of claim 1 wherein the sensor is positioned on the surgical instrument, and wherein receiving light from the portion of tissue and transmitting the received light to the sensor includes transmitting the received light to the sensor.

11. The method of claim 1, wherein the received light is light reflected from the portion of tissue.

12. The method of claim 1, wherein the received light is light emitted by the portion of tissue.

* * * * *